(12) United States Patent
DaCosta

(10) Patent No.: US 10,856,918 B2
(45) Date of Patent: Dec. 8, 2020

(54) MOVEABLE BONE PLATE IMPLANTATION SYSTEM AND METHOD OF USE

(71) Applicant: PARAGON 28, INC., Englewood, CO (US)

(72) Inventor: Albert DaCosta, Lone Tree, CO (US)

(73) Assignee: PARAGON 28, INC., Englewood, CO (US)

( * ) Notice: Subject to any disclaimer, the term of this patent is extended or adjusted under 35 U.S.C. 154(b) by 538 days.

(21) Appl. No.: 15/388,827

(22) Filed: Dec. 22, 2016

(65) Prior Publication Data

US 2017/0100175 A1 Apr. 13, 2017

Related U.S. Application Data

(63) Continuation of application No. PCT/US2014/045576, filed on Jul. 7, 2014.

(60) Provisional application No. 62/020,391, filed on Jul. 2, 2014.

(51) Int. Cl.
*A61B 17/80* (2006.01)

(52) U.S. Cl.
CPC ........ *A61B 17/8019* (2013.01); *A61B 17/808* (2013.01); *A61B 17/8057* (2013.01); *A61B 17/8061* (2013.01)

(58) Field of Classification Search
CPC .............. A61B 17/808; A61B 17/8019; A61B 17/8047; A61B 17/1728; A61B 17/025
See application file for complete search history.

(56) References Cited

U.S. PATENT DOCUMENTS

| 9,138,245 B2* | 9/2015 | Mebarak ................ A61B 17/17 |
| 2002/0183755 A1* | 12/2002 | Michelson ......... A61B 17/7059 606/71 |
| 2005/0015093 A1* | 1/2005 | Suh ..................... A61B 17/1728 606/96 |
| 2006/0095044 A1 | 5/2006 | Grady, Jr. et al. |

(Continued)

OTHER PUBLICATIONS

Supplementary European Search Report issued in corresponding European Patent Application No. EP 14896339 dated Jan. 5, 2018.

(Continued)

*Primary Examiner* — Si Ming Ku
(74) *Attorney, Agent, or Firm* — Heslin Rothenberg Farley & Mesiti P.C.; Jacquelyn A. Graff, Esq.

(57) ABSTRACT

The present invention discloses a moveable bone plate implantation system, controlled movement assembly, and method. The moveable bone plate implantation system includes a movement instrument, translation member removeably coupled to the movement instrument, and a bone plate detachably connected to the translation member. The controlled movement assembly includes a translation member and a bone plate. The translation member includes a shaft with a first end and a second end and a head portion at the first end. The head portion includes an engagement groove recessed into the head portion and a lip extending out from a bottom portion of the engagement groove. The bone plate includes an engagement aperture for receiving the engagement groove and the lip engages a bottom surface of the bone plate during translation of the bone plate. A method for moving bones is also disclosed.

15 Claims, 19 Drawing Sheets

(56) References Cited

U.S. PATENT DOCUMENTS

| | | | |
|---|---|---|---|
| 2006/0155298 A1* | 7/2006 | Mueller | A61B 17/1728 606/104 |
| 2007/0173842 A1 | 7/2007 | Abdou | |
| 2009/0088805 A1* | 4/2009 | Leyden | A61B 17/1728 606/280 |
| 2009/0270925 A1 | 10/2009 | Aryan et al. | |
| 2010/0016900 A1 | 1/2010 | Terres et al. | |
| 2011/0166573 A1 | 7/2011 | Wenk et al. | |
| 2014/0012269 A1* | 1/2014 | Bass | A61B 17/64 606/90 |

OTHER PUBLICATIONS

International Search Report and Written Opinion of the International Searching Authority issued in PCT Application No. PCT/US2014/045576 dated Nov. 4, 2014.

* cited by examiner

US 10,856,918 B2

MOVEABLE BONE PLATE IMPLANTATION SYSTEM AND METHOD OF USE

CROSS REFERENCE

This application is a continuation of PCT Application No. PCT/US2014/045576 filed on Jul. 7, 2014, which claims priority benefit under 35 U.S.C. § 119(e) of U.S. provisional application No. 62/020,391 filed Jul. 2, 2014, all of which is incorporated herein by reference in their entirety.

FIELD OF THE INVENTION

The present invention relates generally to the field of orthopedics related to a moveable bone plate implantation system and methods for using the moveable bone plate implantation system.

BACKGROUND OF THE INVENTION

The currently used methods of achieving bone and joint compression utilize screws and ramped compression holes. These current methods depend largely on the quality of the bone to enable compression. The quality of the bone directly affects the amount of compression because when bone quality decreases, this results in the inability to support the purchase of the screw and resultant low level of compression forces being applied. Thus, when bones are of poor quality, the current methods of applying compression forces across a joint are insufficient to achieve optimum results.

Accordingly, the present invention contemplates new and improved systems and methods which overcome the above-referenced problems and others.

SUMMARY OF THE INVENTION

The present invention is directed toward in line compression bone plate systems and methods.

In one aspect, provided herein is a moveable bone plate implantation system. The moveable bone plate implantation system may include, for example, a movement instrument, a translation member removeably coupled to the movement instrument, and a bone plate detachably connected to the translation member.

In another aspect, provided herein is a controlled movement assembly. The controlled movement assembly may include, for example, a translation member and a bone plate detachably connected to the translation member.

In another aspect, provided herein is a method for moving at least one bone. The method include preparing the at least one bone and obtaining a bone plate system. The method may also include aligning a bone plate on the at least one bone and inserting a first fastener through the bone plate and into a first bone of the at least one bone. The method may further include aligning a translation member with an engagement aperture in the bone plate. The method may also include sliding a first alignment guide of a movement instrument over the translation member and coupling the translation member to the first alignment guide. In addition, the method may include inserting a temporary fixation pin through a second alignment guide of the movement instrument to engage a second bone and coupling the temporary fixation pin to the second alignment guide. The method may further include rotating a movement mechanism of the movement instrument to translate the moveable member with respect to the extension member. The method may also include inserting a second fastener into the second bone through the bone plate and removing the temporary fixation pin, movement instrument, and translation member. Further, the method may include closing the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Generally stated, disclosed herein is an embodiment of a translating bone plate system including a movement instrument, translation member, and bone plate. The terms "translating bone plate system," "compression bone plate system," "moveable bone plate system," and "bone plate implantation system" may be used interchangeably herein as they essentially refer to the same system. Further, a method for using the translating bone plate system is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
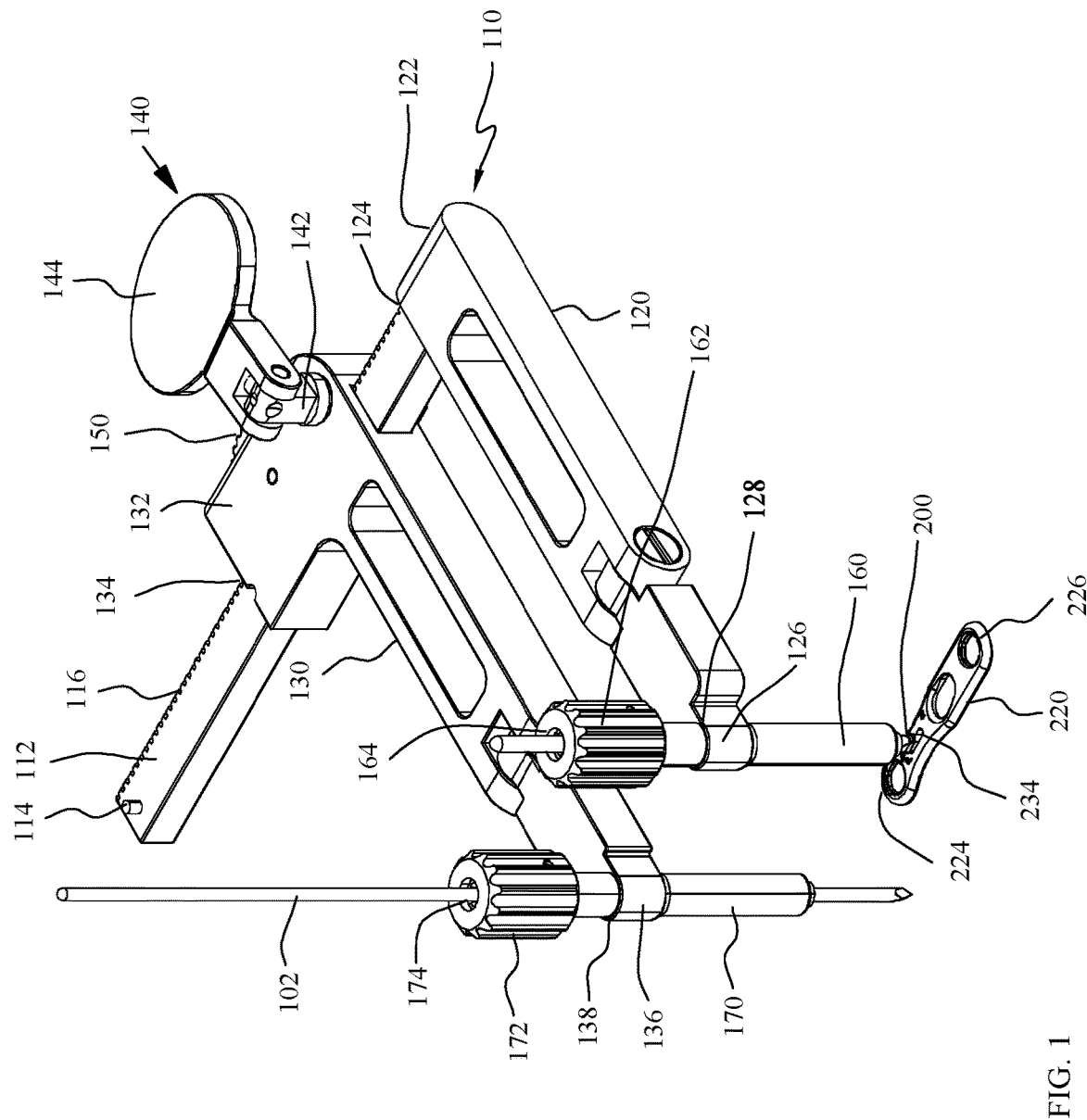
FIG. 1 is a perspective view of a translating bone plate system, in accordance with an aspect of the present invention.
Figure 2:
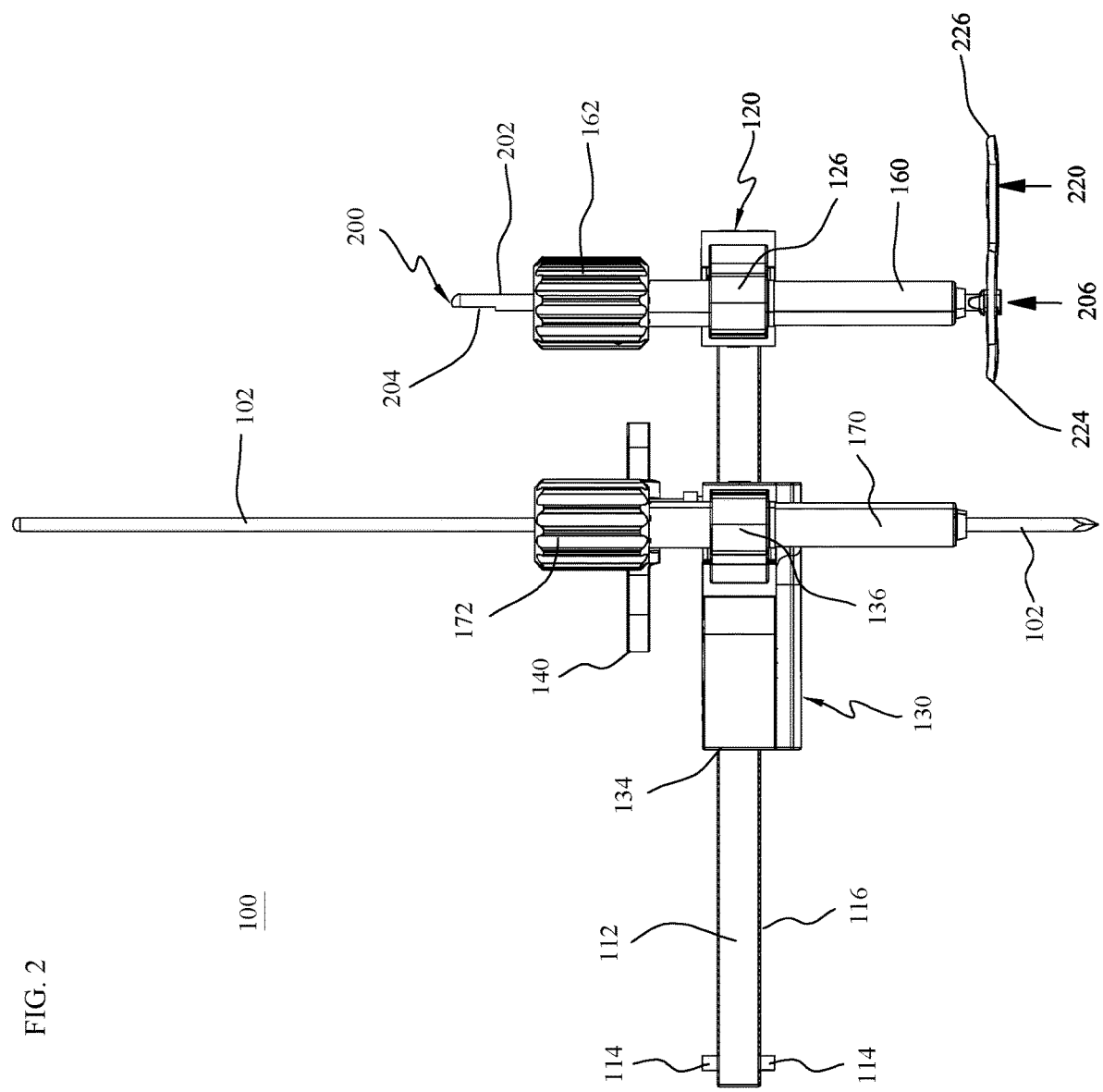
FIG. 2 is a first side view of the translating bone plate system of FIG. 1, in accordance with an aspect of the present invention.
Figure 3:
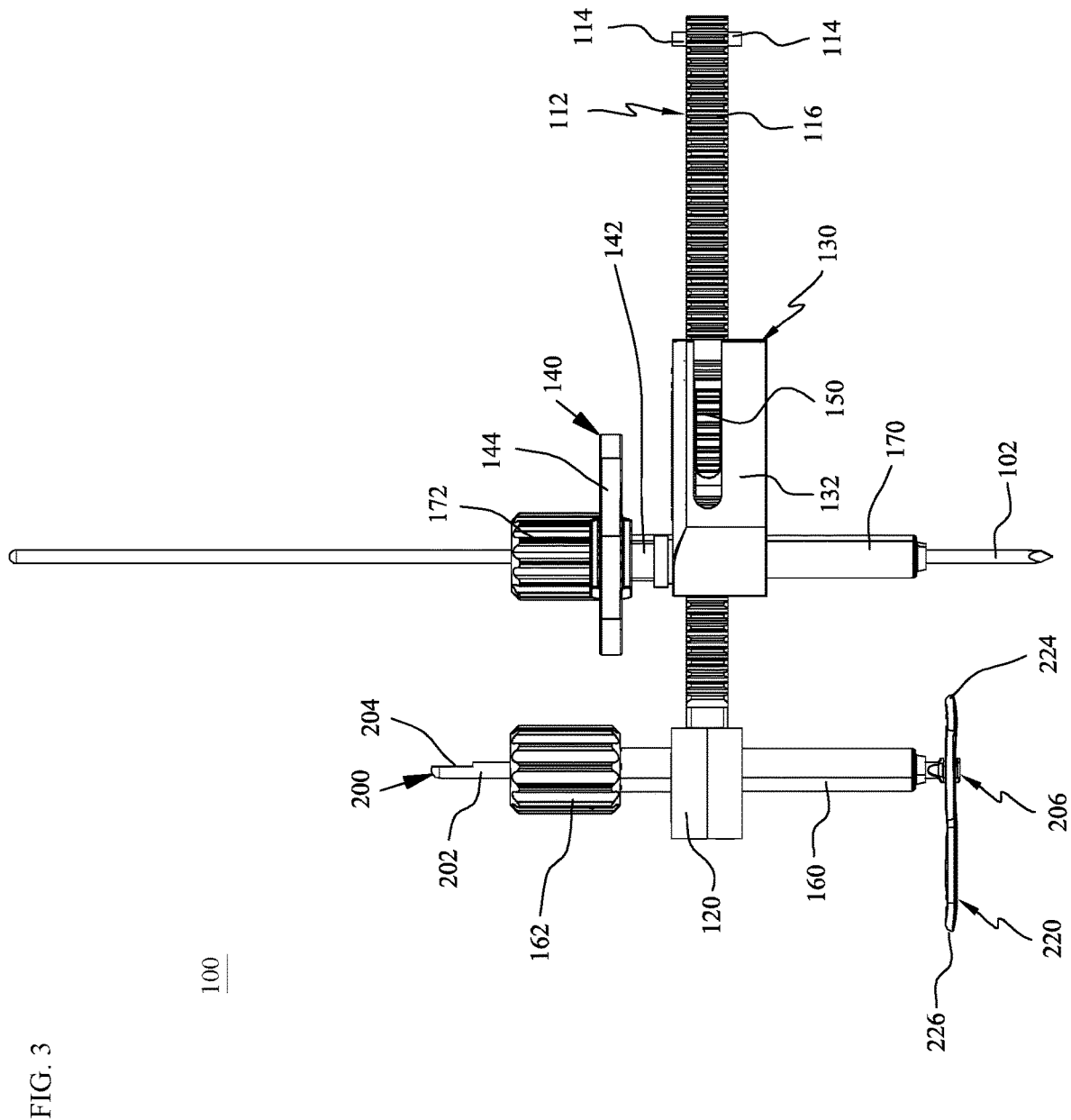
FIG. 3 is a second side view of the translating bone plate system of FIG. 1, in accordance with an aspect of the present invention.
Figure 4:
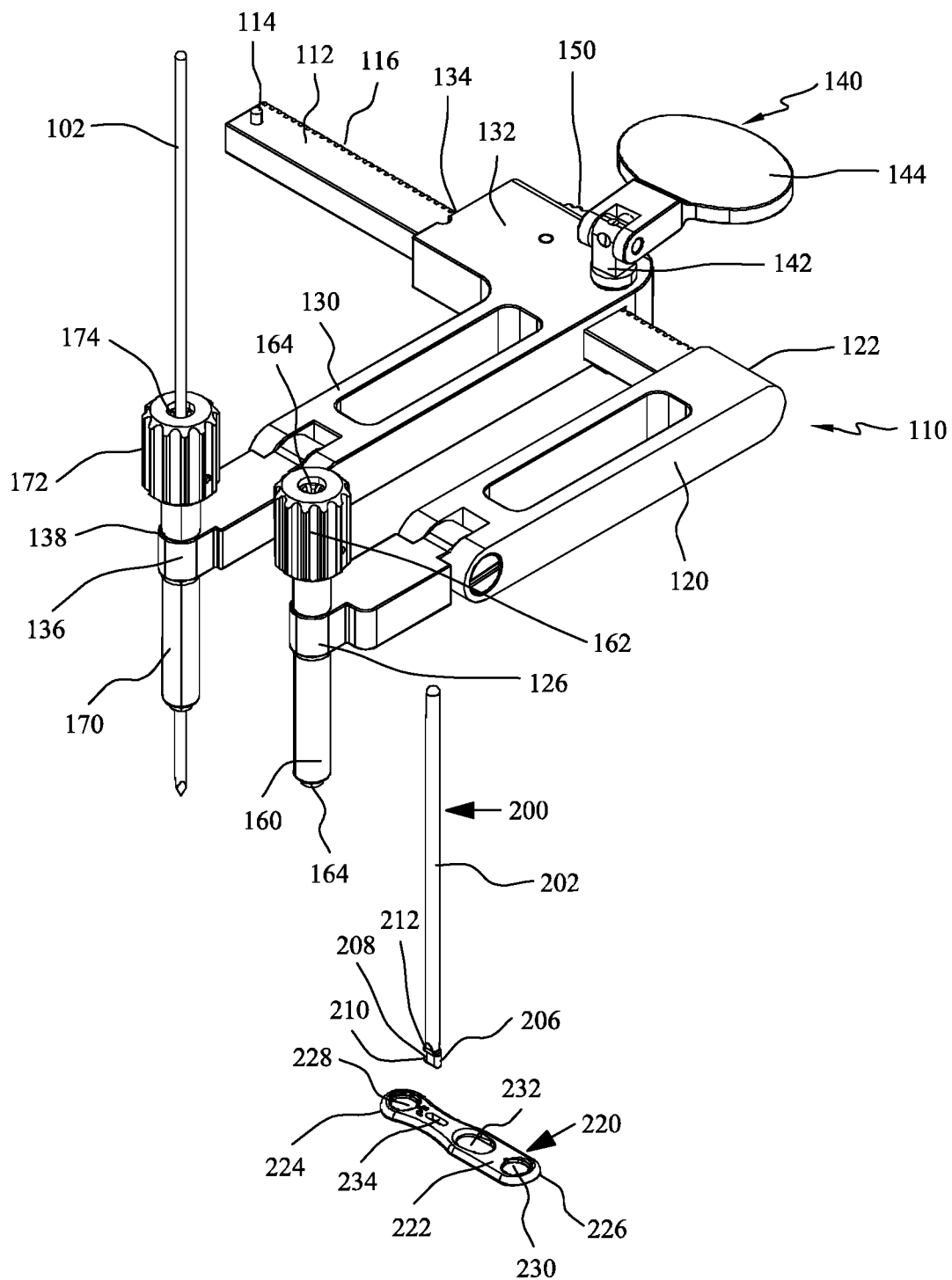
FIG. 4 is a partially exploded perspective view of the translating bone plate system of FIG. 1, in accordance with an aspect of the present invention.
Figure 5:
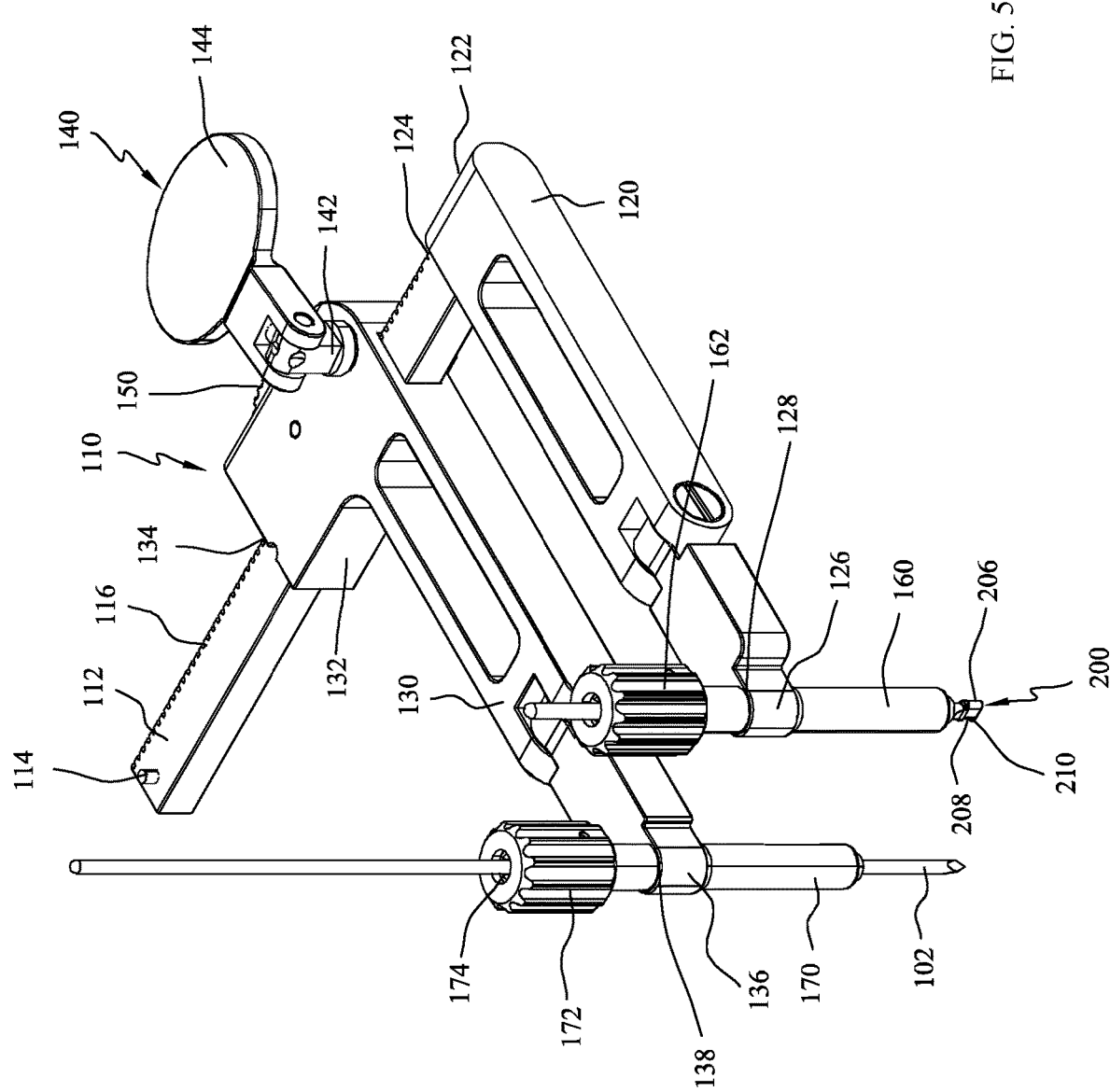
FIG. 5 is a perspective view of the movement instrument and translation member of the bone plate system of FIG. 1, in accordance with an aspect of the present invention.
Figure 6:
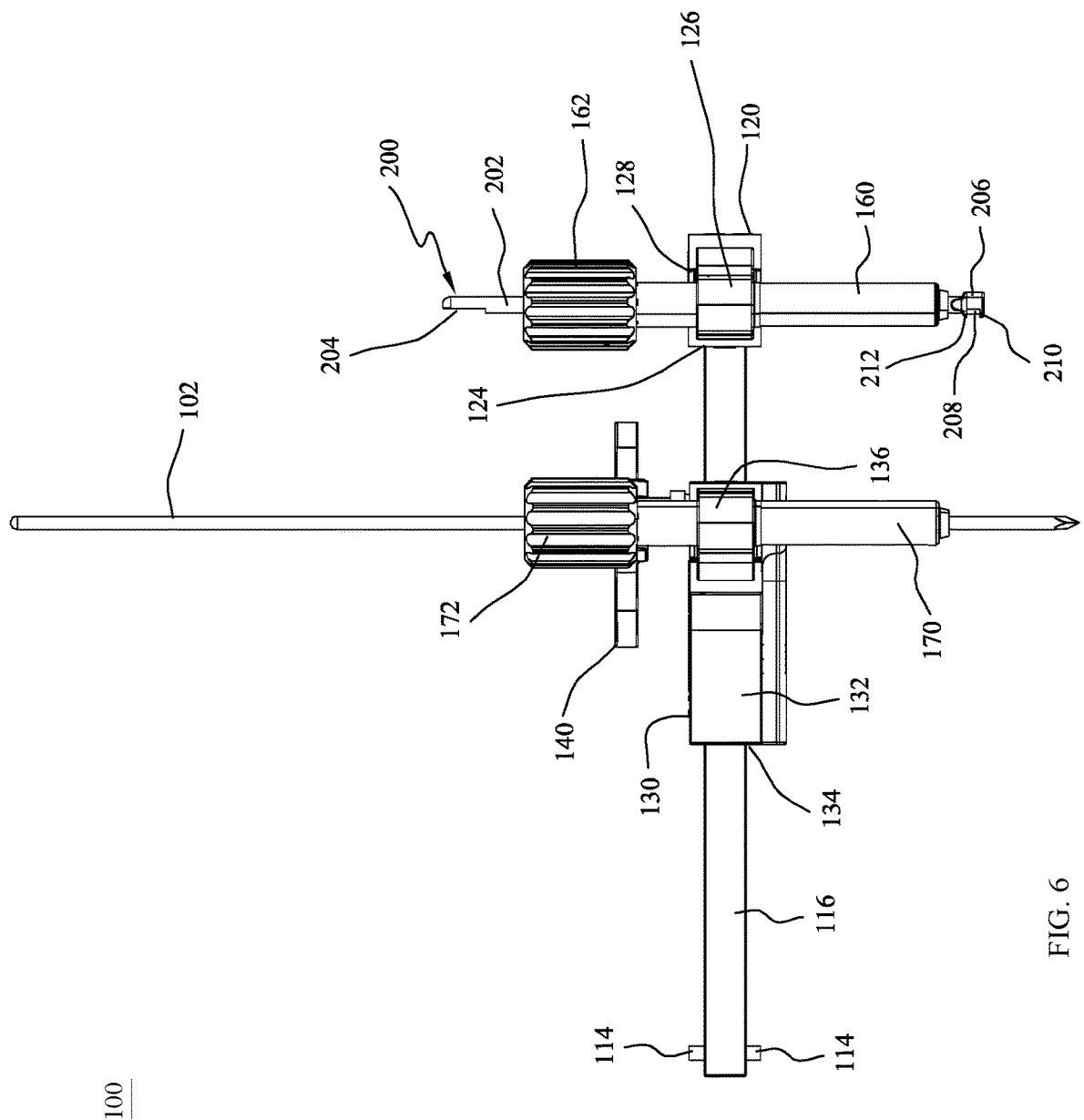
FIG. 6 is a side view of the movement instrument and translation member of the bone plate system of FIG. 1, in accordance with an aspect of the present invention.

Referring to the drawings, wherein like reference numerals are used to indicate like or analogous components throughout the several views, and with particular reference to FIGS. 1-3, one embodiment of a moveable bone plate implantation system 100 is shown. The bone plate system 100 includes a movement instrument 110, a translation member 200, and a bone plate 220. The terms "movement instrument," "compression instrument," and "distraction instrument" may be used interchangeably herein as they essentially refer to the same instrument. The movement instrument 110 may be, for example, similar to commercially available instruments. However, the commercially available instruments do not address plate pivot during movement or changes to positioning of the bones for fusion when a device is off axis during compression.

As seen in FIGS. 1-6, the movement instrument 110 may include, for example, a base member 112, an extension member 120 secured to the base member 112, a moveable member 130 moveably coupled to the base member 112, a first alignment guide member 160, and a second alignment guide member 170. The terms "first alignment guide member" and "first alignment guide" may be used interchangeably herein as they essentially refer to the same member. In addition, the terms "second alignment guide member" and "second alignment guide" may be used interchangeably herein as they essentially refer to the same member. The base member 112 may include at least one stop member 114 at a first end to prevent the moveable member 130 from sliding off the first end of the base member 112. The moveable member 130 may also include a corresponding notch on the top and bottom surface of the moveable member 130 to engage the stop member 114. The base member 112 may also include teeth or a ratchet mechanism 116 on at least one side of the base member 112. The extension member 120 may include a first end 122 with a cavity 124 for receiving a second end of the base member 112. The extension member 120 may also include a second end 126 with an aperture 128 for removably coupling the first alignment guide 160 to the extension member 120. The moveable member 130 may include a first end 132 with an opening 134 for receiving the base member 112 to moveably couple the moveable member 130 to the base member 112. The opening 134 is sized to enable the moveable member 130 to slide along the base member 112 between the stop member 114 and the extension member 120 to compress or distract the attached bones. The moveable member 130 may also include a second end 136 with an aperture 138 for removably coupling the second alignment guide 170 to the moveable member 130.

The moveable member 130 may also include a movement mechanism 140 and a directional switch 150, as shown in FIGS. 1, 3, 4 and 5. The movement mechanism 140 may include a body 142 and a handle 144. The body 142 may include a protrusion or teeth (not shown) to engage the teeth 116 of the base member 112. The protrusion or teeth of the movement mechanism 140 may engage the teeth 116 of the base member 112 as the handle 144 is turned to move the moveable member 130 either toward or away from the extension member 120 to provide the desired compression or distraction. The moveable member 130 moves, for example, linearly along the base member 112. Alternative movement mechanisms 140 may also move the moveable member 130 with respect to the extension member 120. The direction switch 150 may be configured, for example, so that a first position allows the moveable member 130 to move toward a first end of the base member 112 and a second position allows the moveable member 130 to move toward a second end of the base member 112 opposite the first end or vice versa. The direction switch 150 enables the movement instrument 110 to be used for both compression and distraction as desired by the procedure being performed.

Alternative movement instruments 110 including two arms 120, 130 that may be translated to compress or distract the alignment guide members 160, 170 with respect to each other, which are shaped to receive and secure the translation member 200 and a pin 102 for coupling to the first and second bones during compression or retraction, are also contemplated. Further, alternative movement instruments 110 are also contemplated, such as, scissor type movement instruments. The scissor type instruments may include, for example, a first arm, a second arm and a pivot mechanism connecting the first arm and the second arm. The scissor type instruments may also include a first opening in the first arm for receiving the translation member 200 and a second opening in the second arm for receiving the pin 102. The scissor type instruments may allow for compression or distraction of the bones coupled to the translation member 200 and the pin 102. The scissor type instruments may also include securement mechanisms to secure the translation member 200 and the pin 102 to the first and second openings in the first and second arms. Further, the scissor type instruments may also include a locking mechanism to hold the scissors in a given position once the desired compression or distraction is reached so that a second fastener may be inserted through the bone plate 220.

As shown in FIGS. 1-6, the first and second alignment guide members 160, 170 each include a locking knob 162, 172 at a first end of the alignment guides 160, 170 and through holes 164, 174 extending through the guides 160, 170 along a longitudinal axis of the guides 160, 170. The hole 164 may receive the translation member 200 after it is inserted to engage the bone plate 220. The translation member 200 may be secured in the desired position with respect to the movement instrument 110 by turning knob 162 to, for example, extend at least one tab or finger (not shown) to engage the translation member 200 and hold the translation member 200 in the desired position during translation of the bones. The hole 174 may receive the temporary fixation pin or guide wire 102 as it is inserted into a bone (not shown). The pin 102 may be secured in the desired position by turning the knob 172 to, for example, extend at least one tab or finger (not shown) to engage the pin 102 to hold the pin 102 in a desired position during translation of the bones. The translation member 200 could also be inserted into hole 174 and the pin 102 could be inserted into hole 164 as necessary to correspond to the orientation of the patient. Alternative locking mechanisms 162, 172, such as a set screw or clamping collar, to secure the translation member 200 and the pin 102 in the alignment guides 160, 170 are also contemplated.

In further embodiments, it is also contemplated that the movement instrument 110 may include alignment guides 160, 170 that do not contain locking mechanisms. If the movement instrument 110 lacks locking mechanisms in the alignment guides 160, 170, then the translation member 200 and pin 102 may be positioned in the alignment guides 160, 170 and compression or distraction performed with the alignment guides 160, 170 retaining the translation member 200 and pin 102 within the holes 164, 174. Movement instruments 110 that lack locking mechanisms in the alignment guides 160, 170 could also be used by securing the translation member 200 and/or pin 102 to the alignment guides 160, 170 by bending the translation member 200 and/or pin 102 over the movement instrument 110 to prevent the translation member 200 and/or pin 102 from sliding out of the movement instrument 110 during compression or distraction.

The first alignment guide 160 may be positioned in the aperture 128 of the extension member 120 and the second alignment guide 170 may be positioned in the aperture 138 of the moveable member 130, as shown in FIGS. 1, 2, and 4-6. The first and second alignment guides 160, 170 may be sized to securely fit into the apertures 128, 138.

Figure 7:
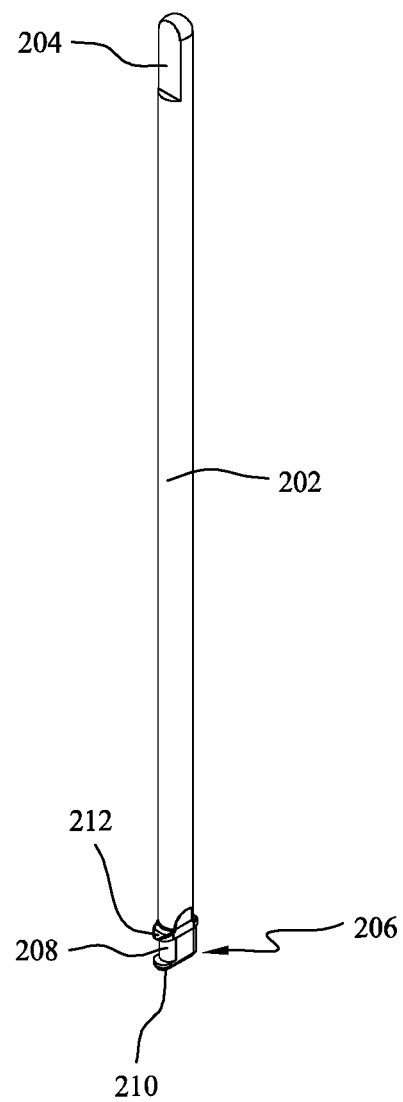
FIG. 7 is a perspective view of the translation member of the bone plate system of FIG. 1, in accordance with an aspect of the present invention.
Figure 8:
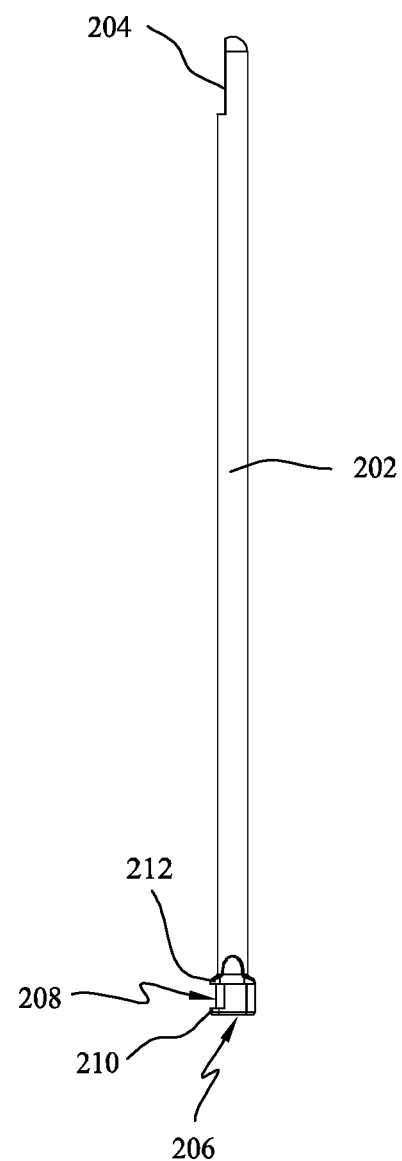
FIG. 8 is a side view of the translation member of the bone plate system of FIG. 1, in accordance with an aspect of the present invention.
Figure 9:
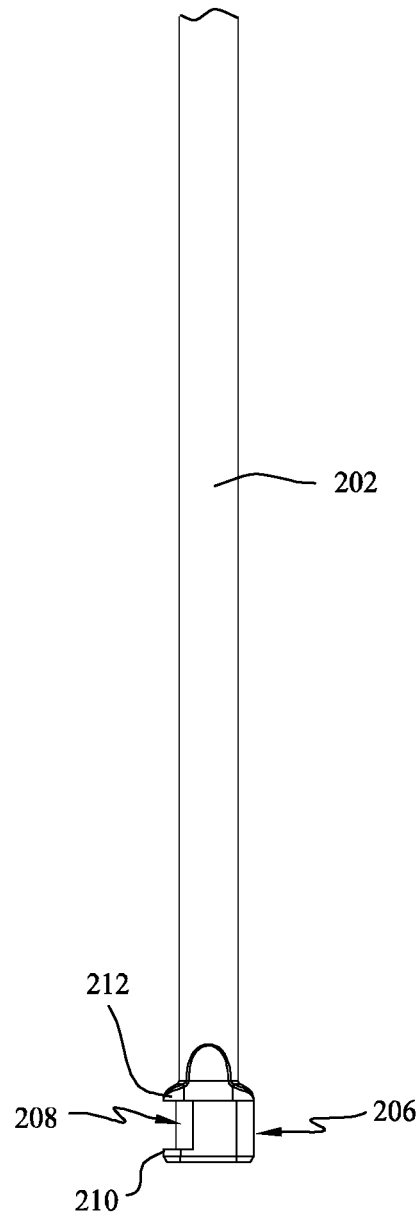
FIG. 9 is an enlarged side view of a portion of the translation member of the bone plate system of FIG. 1, in accordance with an aspect of the present invention.

Referring now to FIGS. 7-9, the translation member 200 may include, for example, a shaft 202 and a head portion 206. The terms "translation member," "compression member," and "distraction member" may be used interchangeably herein as they essentially refer to the same device. The shaft 202 may include a cutout 204 at a first end for engaging an insertion instrument (not shown). The head portion 206 may be positioned at a second end opposite the cutout 204. The head portion 206 may include an engagement groove 208 for aligning with the bone plate 220, a first lip 210 at the bottom of the engagement groove 208 to engage a bottom surface of the bone plate 220, and a second lip 212 at the top of the engagement groove 208 to engage a top surface of the bone plate 220. The first and second lips 210, 212 also hold the bone plate 220 in place. The engagement groove 208 may be recessed into the head portion 206 and may have a height that corresponds to the thickness of the bone plate 220 that the translation member 200 is engaging for translation. The height of the engagement groove 208 is sized to match the thickness of the bone plate 220 to allow for only a little movement and to prevent pivoting of the bone plate 220. The height of the engagement groove 208 may be, for example, approximately 1 mm to 2 mm. The lips 210, 212 may extend away from the engagement groove 208. The lip 210 may provide a surface for mating with the bottom surface 238 of the bone plate 220. The lips 210, 212 may have a length of, for example, approximately 0.3 mm to 0.6 mm. The engagement groove 208 may be fixed or adjustable. An adjustable engagement groove 208 includes an adjustment mechanism (not shown) that allows for movement of the second lip 212 with respect to the first lip 210 to move the second lip 212 toward or away from the first lip 210 to increase or decrease the thickness of the engagement groove 208.

Figure 10:
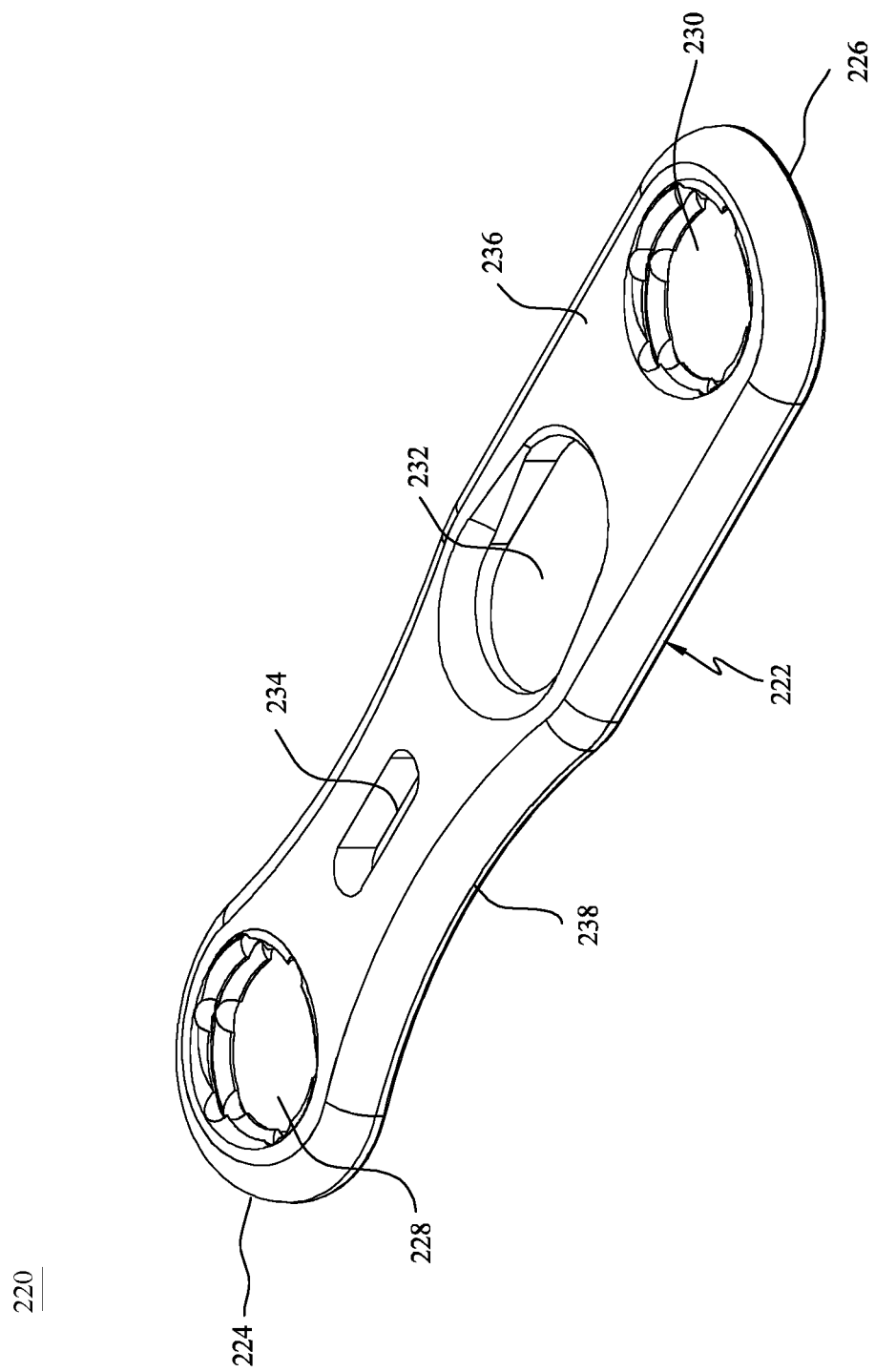
FIG. 10 is a perspective view of the bone plate of the bone plate system of FIG. 1, in accordance with an aspect of the present invention.
Figure 11:
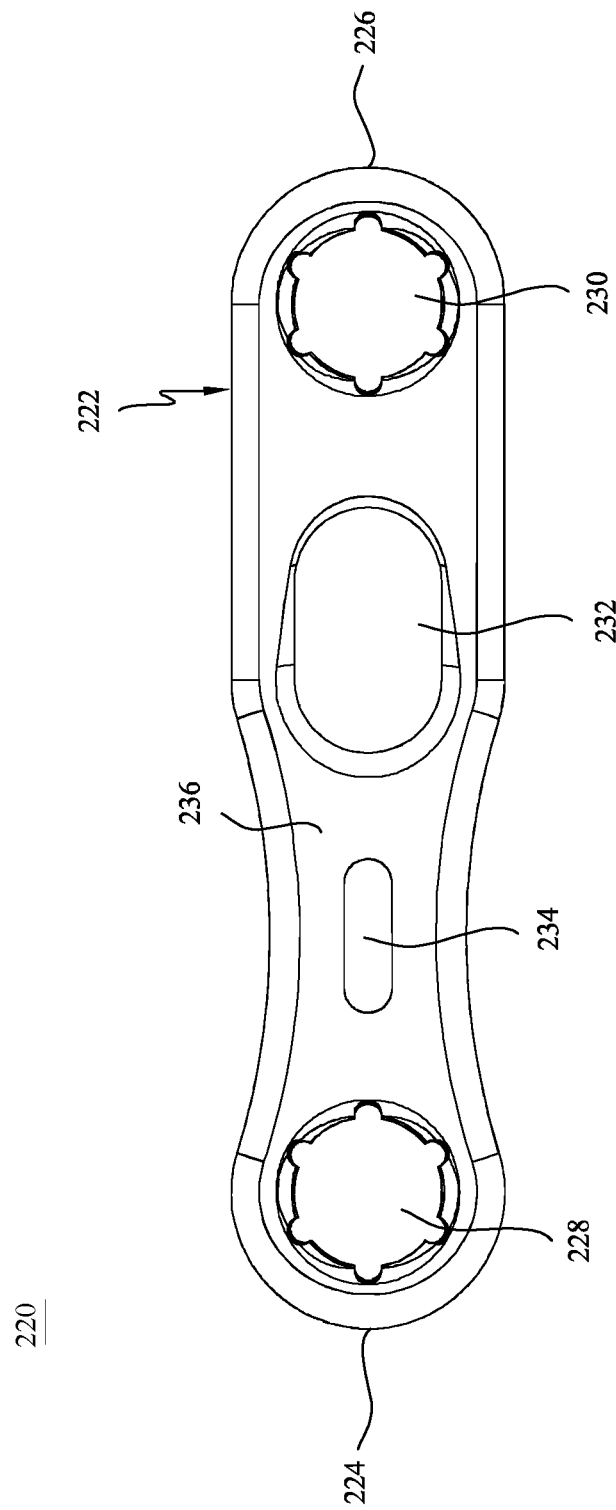
FIG. 11 is a top view of the bone plate of the bone plate system of FIG. 1, in accordance with an aspect of the present invention.

The bone plate 220 is shown in FIGS. 10 and 11. The bone plate 220 may include, for example, a body 222 with a first end 224 and a second end 226. The bone plate 220 may also include, at least one first hole 228 near the first end 224 and at least one second hole 230 near the second end 226. The bone plate 220 may also optionally include at least one slot 232 which may be, for example, a compression slot for receiving a bone screw (not shown) to apply additional compression between the two bones. In addition, the bone plate 220 may also include an engagement aperture 234 for receiving the head portion 206 of the translation member 200. Although the engagement aperture 234 is shown as an oval or rectangular shaped configuration, it is also contemplated that the engagement aperture 234 may have a triangular, square, or other polygonal shaped configuration, which may match the shape of the engagement groove 208. The at least one first hole 228, at least one second hole 230, at least one slot 232, and engagement aperture 234 may each extend from a top surface 236 of the bone plate 220 through to a bottom surface 238 of the bone plate 220. The bone plate 220 is shown as a rectangular or oval shaped plate, however, any sized and shaped plate may be used with the movement instrument 110. The bone plate 220 may have a width extending between the top surface 236 and the bottom surface 238 of the engagement aperture 234. The width of the bone plate 220 near the engagement aperture 234 may be, for example, approximately 1.5 mm to 2.5 mm. The bone plate 220 may include a bottom groove (not shown) opening into the engagement aperture 234 for receiving the lip 210. The bottom groove and lip 210 may have corresponding shapes. Alternatively, a chamfer may be placed on the bottom surface 238 of the bone plate 220 opening into the engagement aperture 234 for receiving the lip 210. The chamfer may be shaped to match the shape of the head portion 206.

Figure 15:
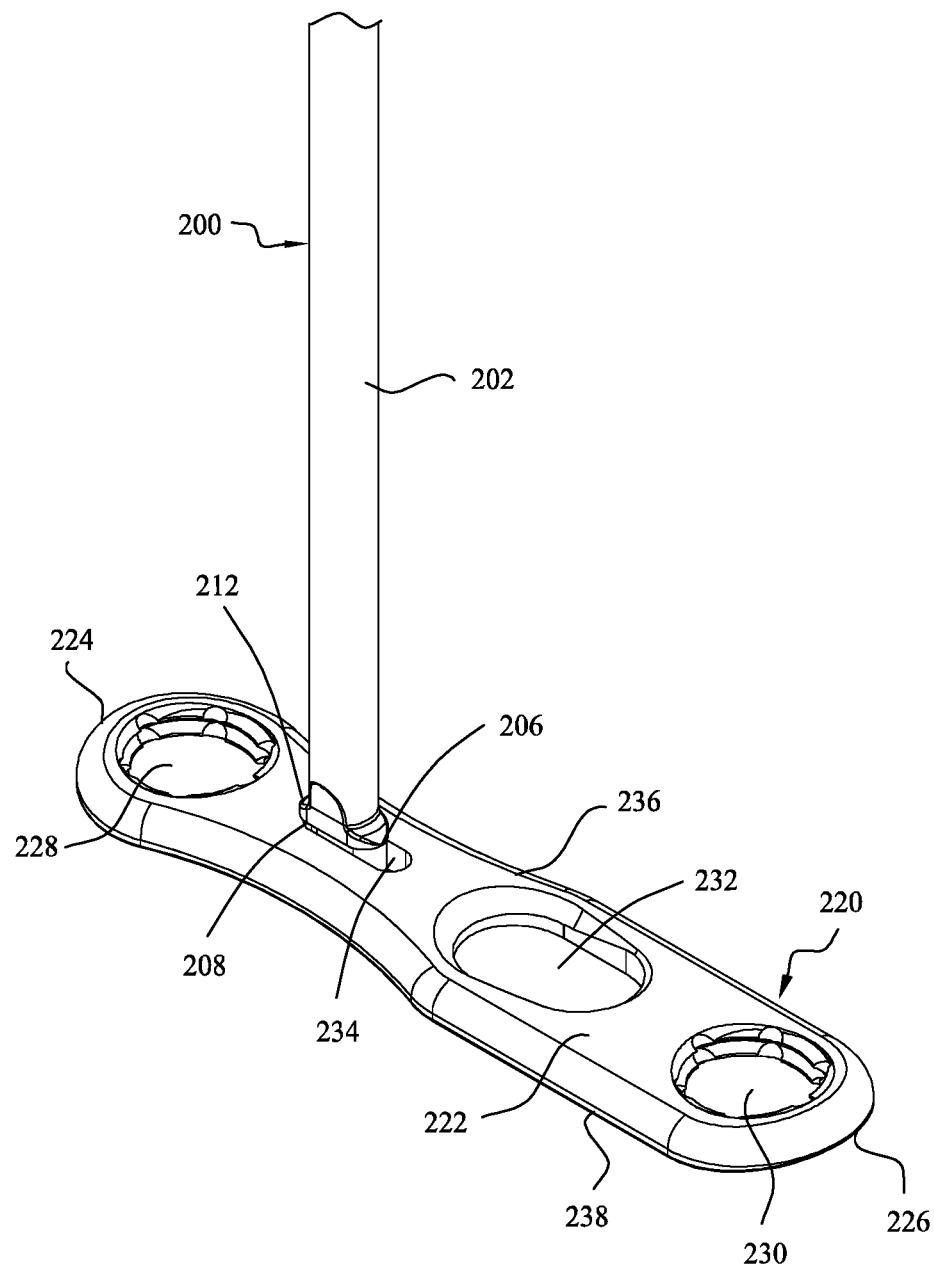
FIG. 15 is a perspective view of the bone plate and a portion of the translation member of the bone plate system of FIG. 1, in accordance with an aspect of the present invention.
Figure 16:
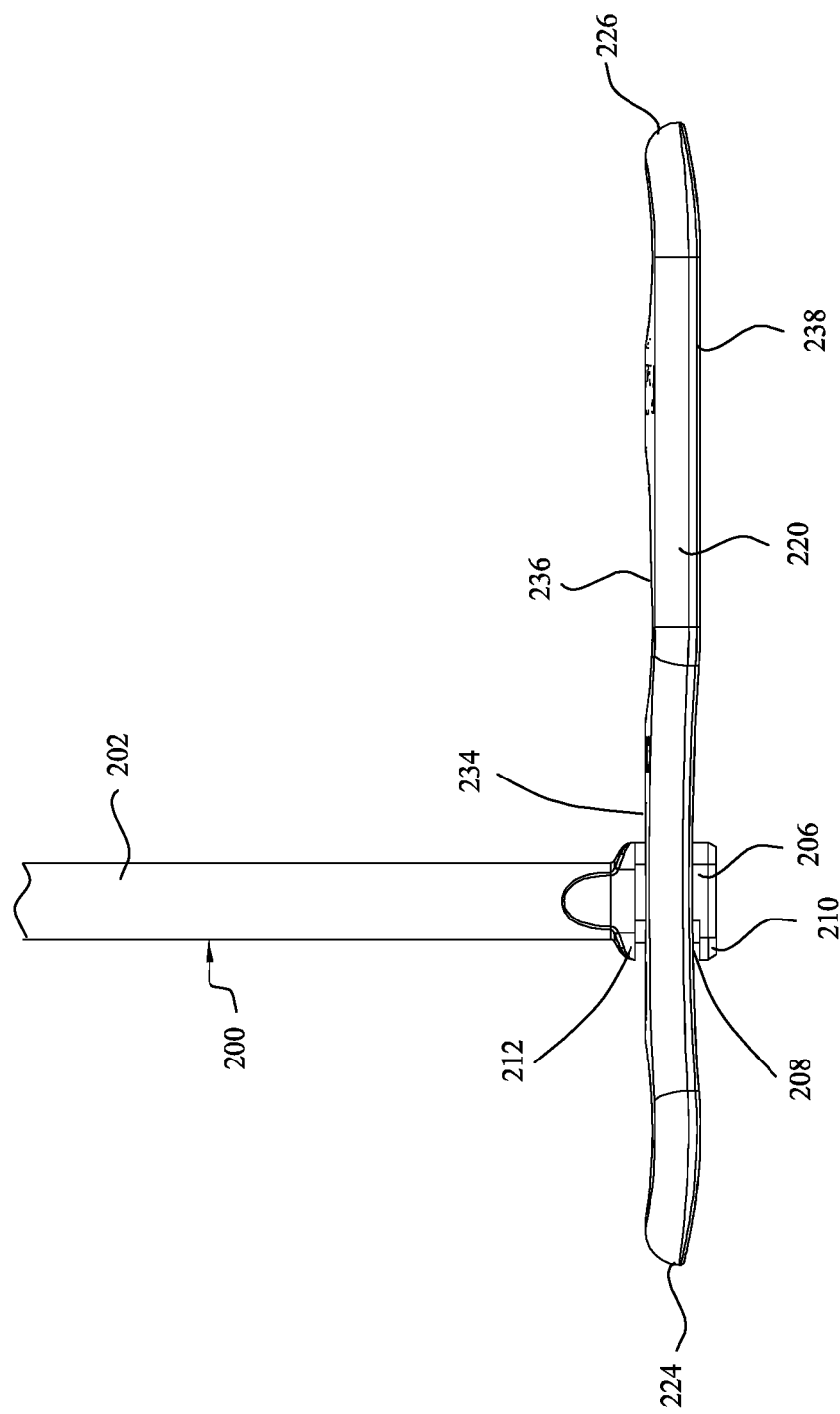
FIG. 16 is a side view of the bone plate and a portion of the translation member of the bone plate system of FIG. 1, in accordance with an aspect of the present invention.

FIGS. 15 and 16 show a controlled movement assembly including the translation member 200 and the bone plate 220. Although described herein as being used with the movement instrument 110, it is also contemplated that alternative movement instruments may be used. An alternative movement instrument 110 would need to receive the controlled movement assembly and allow the controlled movement assembly to couple to the bone plate 220 for controlled movement of two bones with respect to each other as described in greater detail below. It is also contemplated that alternative bone plates 220 which include an engagement aperture 234 may be used with the translation member 200 and a movement instrument 110.

Figure 17:
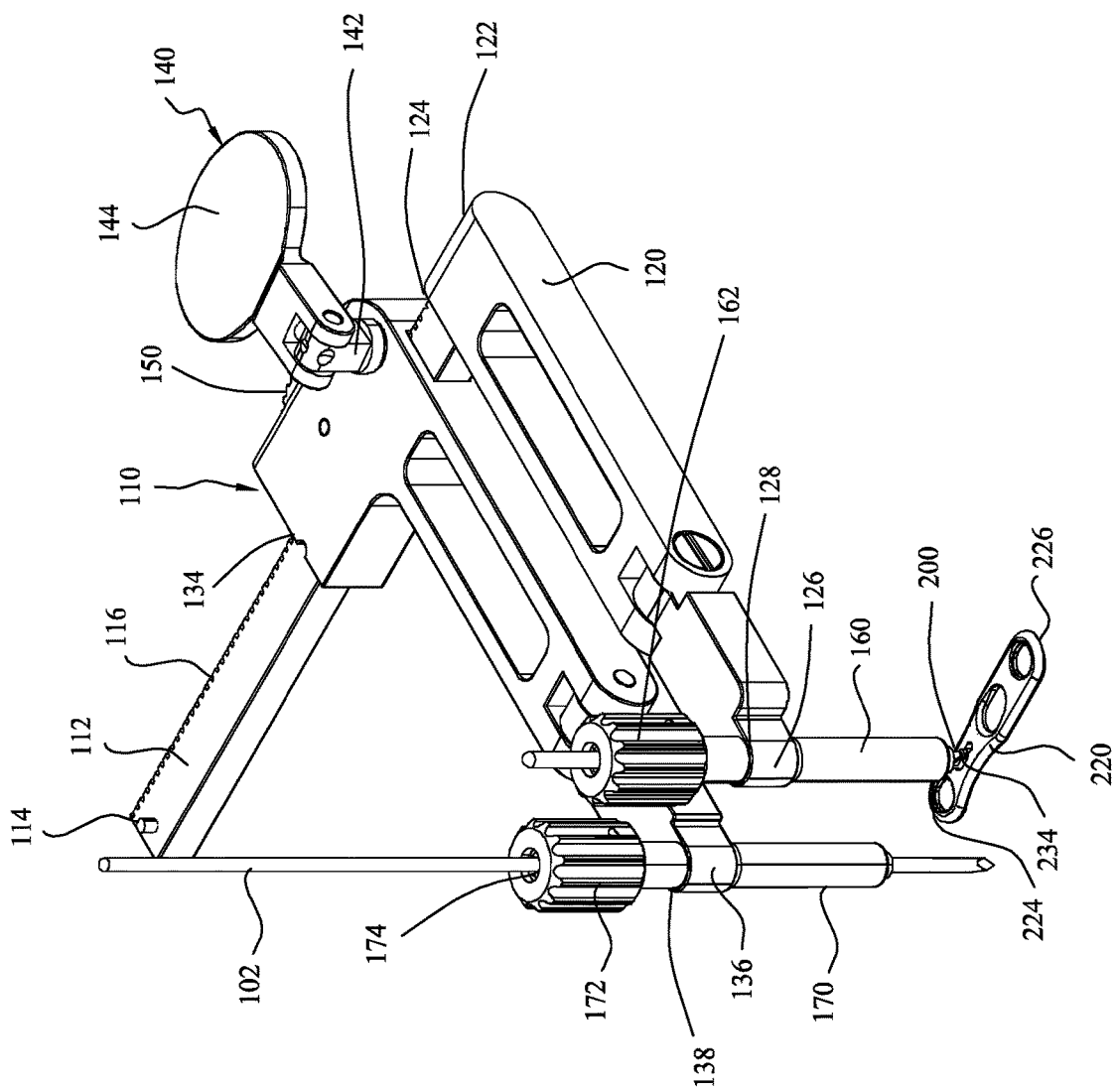
FIG. 17 is a perspective view of the bone plate system of FIG. 1 in a second position, in accordance with an aspect of the present invention.
Figure 18:
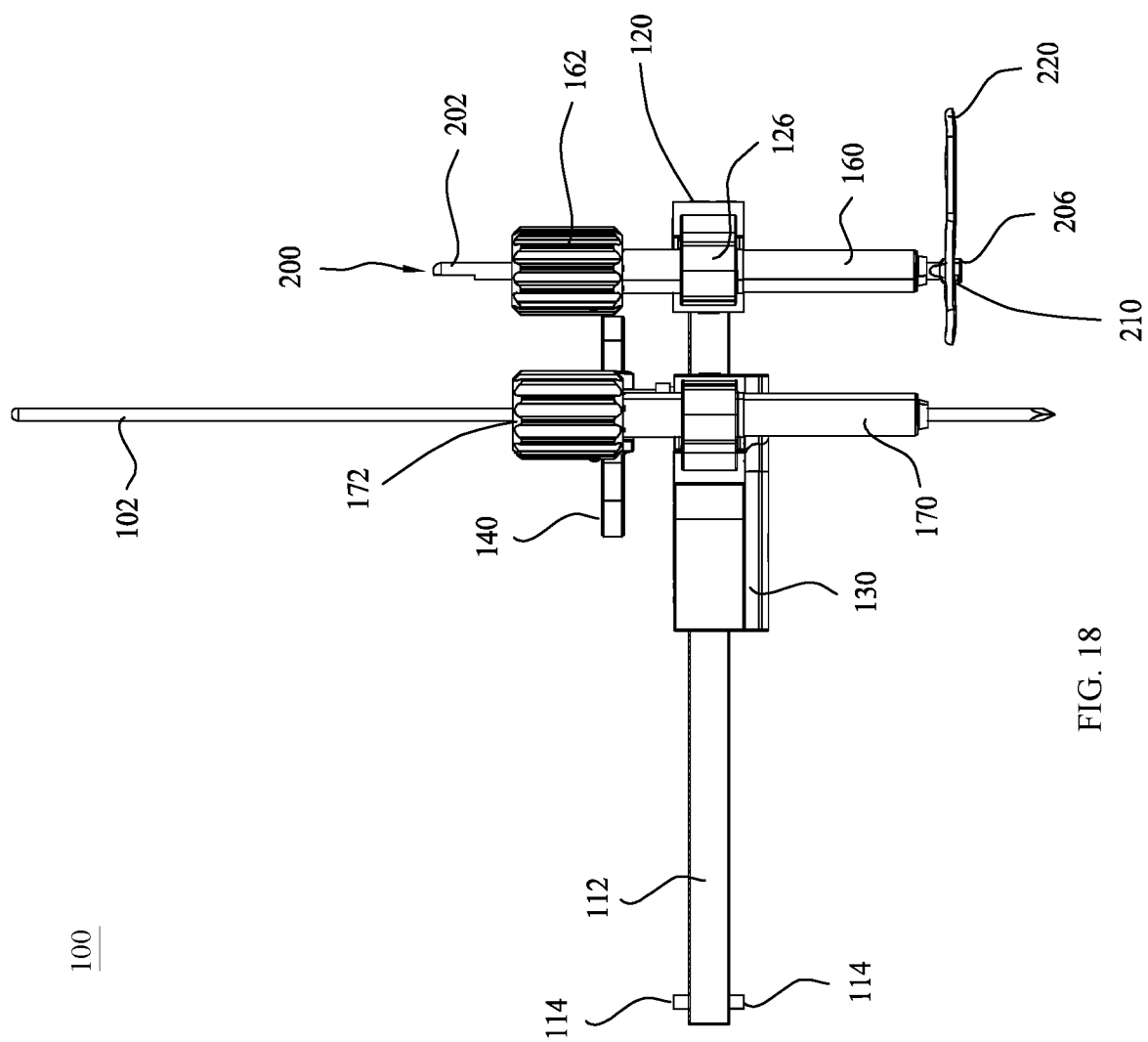
FIG. 18 is a first side view of the bone plate system of FIG. 17, in accordance with an aspect of the present invention.
Figure 19:
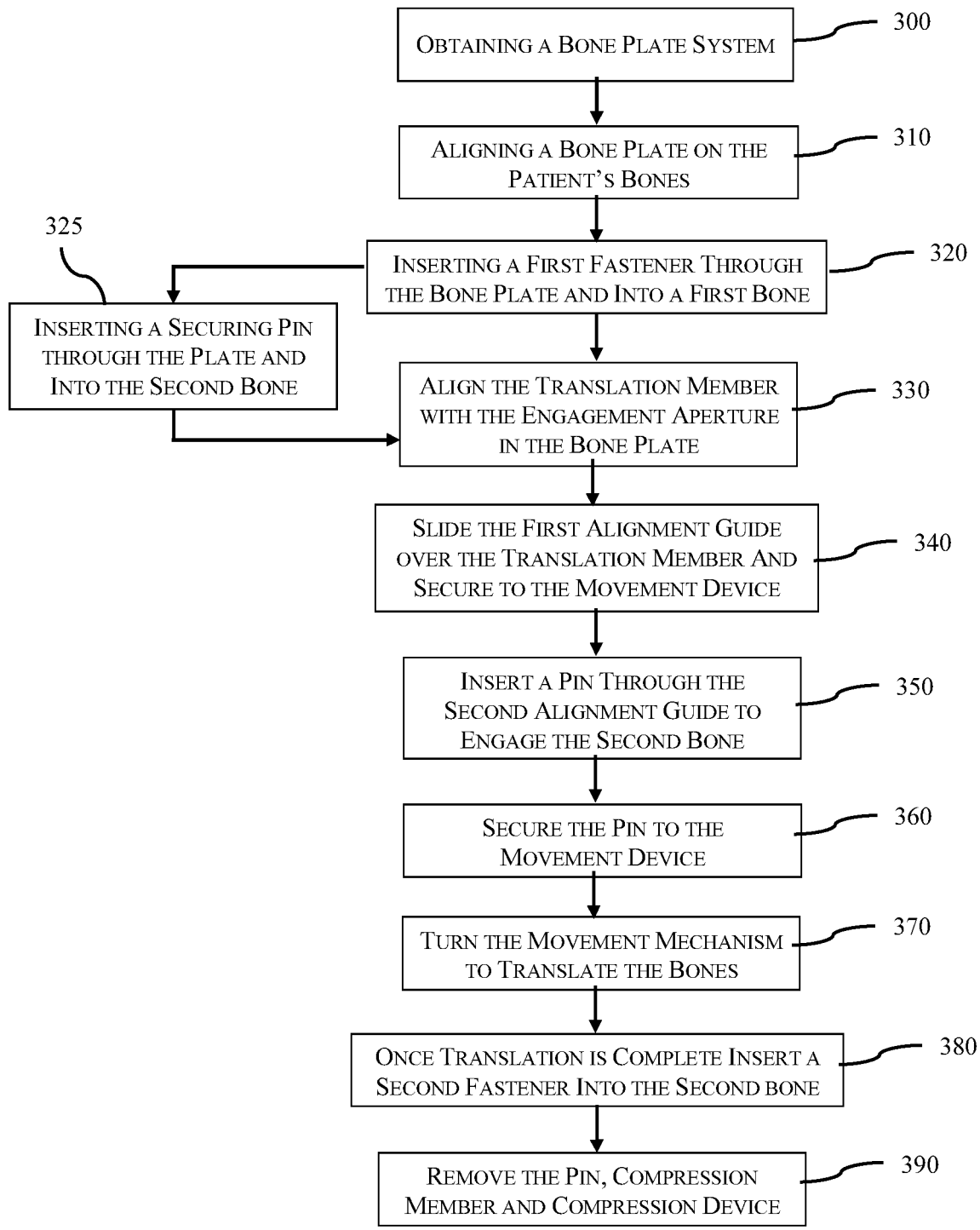
FIG. 19 depicts one embodiment of a method for using the translating bone plate system, in accordance with an aspect of the present invention.

Referring now to FIGS. 12-19, the method of using the moveable bone plate implantation system 100 is shown. As illustrated in FIG. 19, the method may include creating an incision and resultant surgical opening on the patient where the joint compression is needed, for example, a patient's foot, and preparing the site. The method may also include obtaining a moveable bone plate implantation system 300 including, for example, a movement instrument 110, a translation member 200, and a bone plate 220. The method may further include, for example, aligning the bone plate on the patient's bones 310 and inserting a first fastener through the bone plate and into a first bone 320. The method may also optionally include, for example, inserting a temporary fixation pin through the at least one second hole and into the second bone 325. The temporary fixation pin may be, for example, a securing pin, an olive wire, or the like to hold the bone plate 220 in the desired position until the pin 102 is inserted through the movement instrument 110 and into the second bone (not shown). Next the method may include, for example, aligning the translation member with the engagement aperture in the bone plate 330, as shown in FIGS. 12-16. The method may further include, for example, sliding the first alignment guide over the translation member and securing the first alignment guide to the movement instrument 340. The method may also include, for example, inserting a pin through the second alignment guide to engage the second bone 350 and securing the pin to the movement instrument 360. In addition, the method may include, for example, turning the movement mechanism to translate the bones 370. The translation of the bones may be, for example, to compress the two bones together or distract the two bones apart. Once the desired movement, such as compression as shown in FIGS. 17-18, is complete the method may also include inserting a second fastener into the second bone through the bone plate 380. Finally, the method may include removing the pin, compression member, and compression device from the patient 390 and closing the incision.

Figure 12:
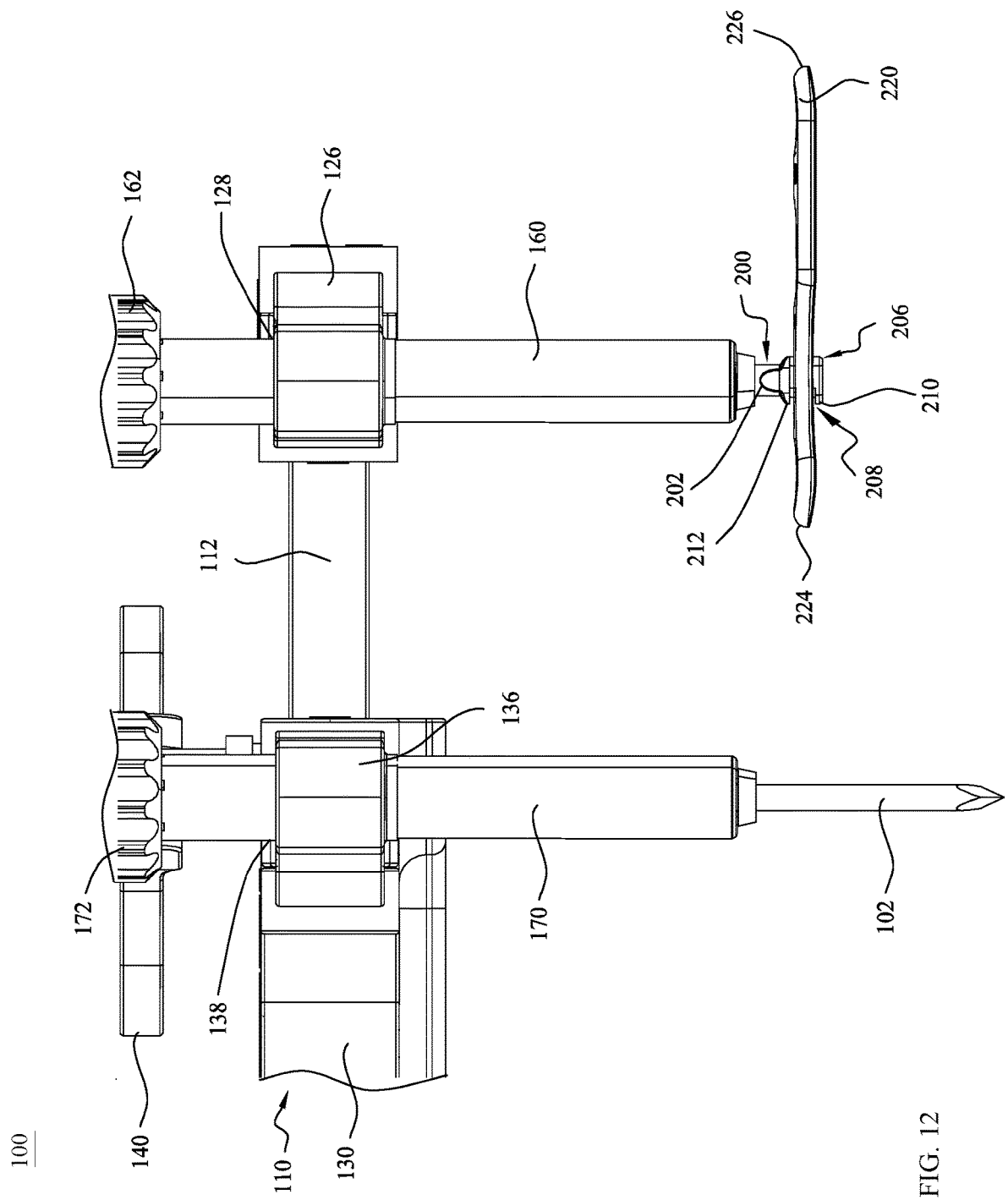
FIG. 12 is a side view of a portion of the bone plate system of FIG. 1, in accordance with an aspect of the present invention.
Figure 13:
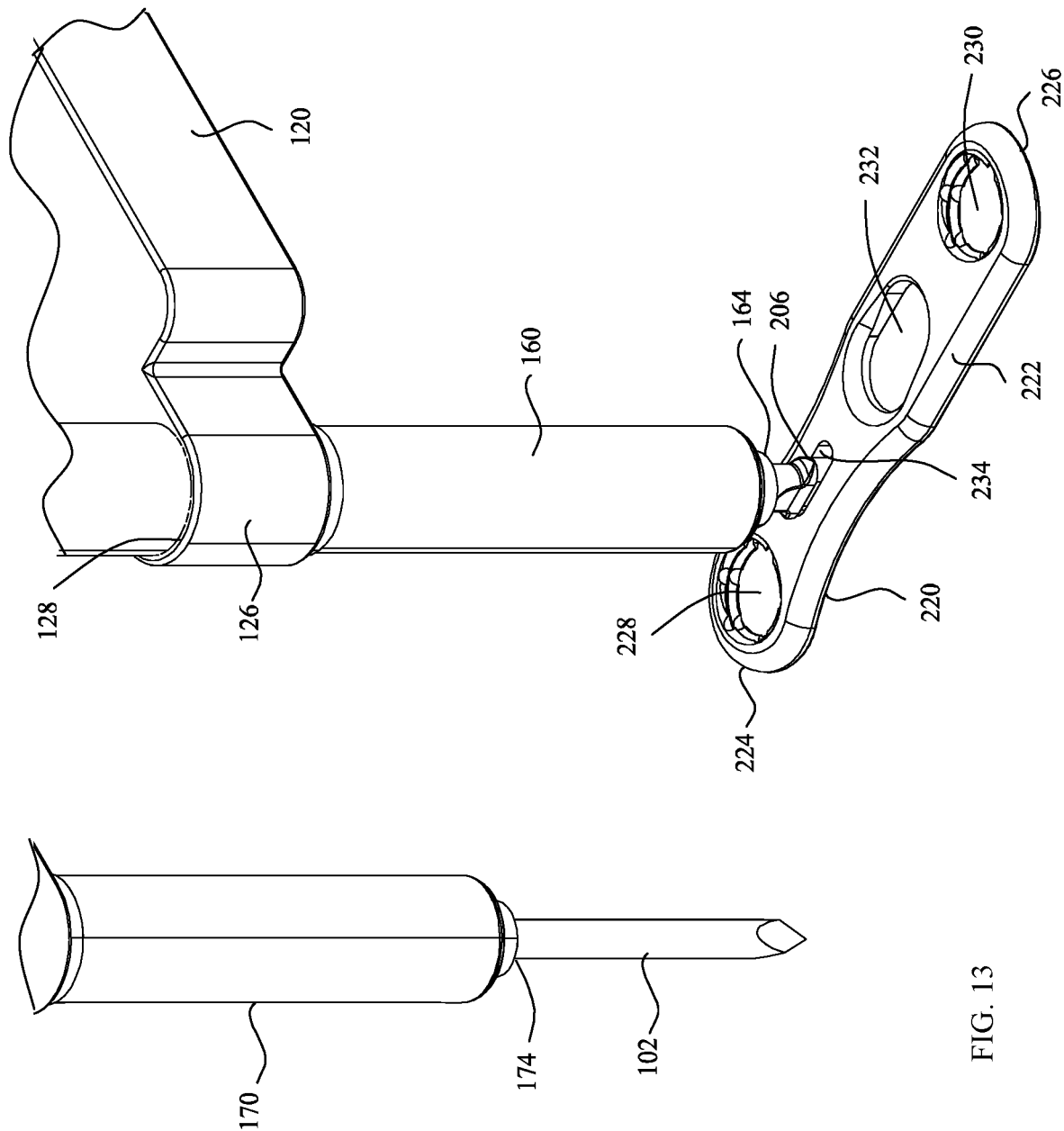
FIG. 13 is a perspective view of a portion of the bone plate system of FIG. 1, in accordance with an aspect of the present invention.
Figure 14:
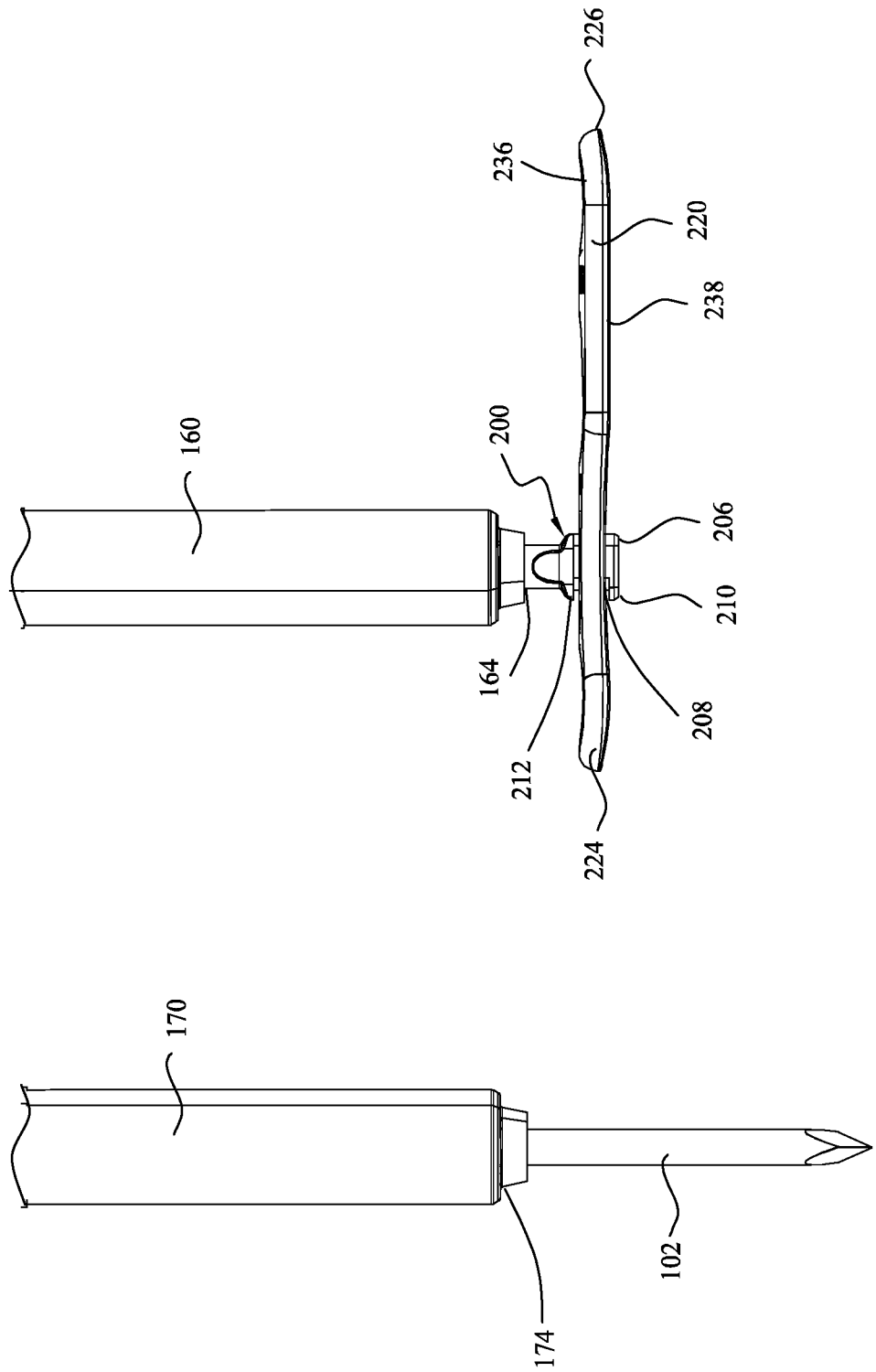
FIG. 14 is a side view of a portion of the bone plate system of FIG. 1, in accordance with an aspect of the present invention.

The method as shown in FIG. 19 may be described in greater detail with reference to FIGS. 1-4 and 12-18. Once the bone plate 220 is attached to a first bone (not shown) with a first fastener (not shown), a temporary fixation device (not shown) may then be inserted into a second bone (not shown) through a hole 228 on the opposite side of the plate. The first fastener may be, for example, a locking screw or non-locking screw. A locking screw may be used to prevent rotation of the screw during movement of the bone plate 220. The temporary fixation device may be used to hold the bone plate 220 in a desired position on the second bone during attachment of the movement instrument 110. Next the translation member 200 may be aligned and engaged with the engagement aperture 234 of the bone plate 220, as shown in FIGS. 1-3 and 12-18. The translation member 200 mates with the bone plate 220 by engaging the engagement groove 208 of the translation member 200 with the edge of the engagement aperture 234 of the bone plate 220, as shown in FIGS. 15 and 16. When the engagement groove 208 mates with the engagement aperture 234, the lips 210, 212 of the head portion 106 of the translation member 200 overlap the body 222 of the bone plate 220, as shown in FIGS. 12, 14, and 16. For example, the lip 210 may overlap the body 222 on a bottom surface 238 of the bone plate 220 and the lip 212 may overlap the body 222 on a top surface 236. Overlapping of the lip 210 of the translation member 200 with the body 222 of the bone plate 220 may prevent the translation member 200 from disengaging or popping off the bone plate 220 during translation. As shown in the depicted embodiment, for compression, the engagement groove 208 may be positioned in the engagement aperture 234 nearest the first end 224 of the bone plate 220, as shown in FIGS. 1-3 and 12-18. Alternatively, for distraction, the engagement groove 208 may be positioned in the engagement aperture 234 nearest the second end 226 of the bone plate 220.

Next the first alignment guide 160 of the movement instrument 110 may be slid over the translation member 200 by aligning the translation member 200 with the through hole 164. Once the first alignment guide 160 is in the desired position with respect to the translation member 200, the knob 162 may be turned to secure the translation member 200 in the through hole 164 of the first alignment guide 160. Then the second alignment guide 170 of the movement instrument 110 may be aligned with the second bone (not shown) and a temporary fixation pin 102 may be inserted into the second bone. The pin 102 may be inserted through the through hole 174 in the second alignment guide 170 and into the second bone (not shown). Once the pin 102 is inserted into the second bone in the desired position, the knob 172 of the second alignment guide 170 may be rotated to lock the pin 102 in the desired position. The alignment guides 160, 170 may be pivoted near the second ends 126, 136 of the two arms 120, 130 to converge the translation member 200 and pin 102 slightly towards each other. By rotating the translation member 200 and pin 102 slightly towards each other, converging compression may be applied to better distribute the forces across the joint or fusion site. For example, the translation member 200 may be inserted at 90 degrees and the pin 102 may be angled to converge with the translation member 200 to better distribute forces across the fusion site and prevent gapping of counter side of the fusion site. After the pin 102 is secured to the movement instrument 110, the bone plate implantation system 100 has been assembled, as shown in FIGS. 1-3, and is ready to translate the two attached bones (not shown).

Then the handle 144 of the movement mechanism 140 may be turned or rotated to move the moveable member 130 along the base member 112. As the handle 144 is turned the teeth or protrusions (not shown) on the body 142 of the movement mechanism 140 engage the teeth 116 on the base member 112 and translate the movement mechanism 140 along the base member 112. The movement mechanism 140 may be, for example, a rack and pinion type mechanism. As shown in FIGS. 17 and 18, the moveable member 130 may translate towards the extension member 120 as the movement mechanism 140 is rotated causing compression of the attached bones (not shown). The moveable bone plate implantation system 100 allows for translation, for example, compression, of the attached bones in line with the bone plate 220. The in line movement may, for example, avoid pulling bones out of alignment. Once the translation of the moveable member 130 has achieved the desired compression, a second fastener (not shown) may be inserted into the second bone (not shown) through the bone plate 220 to secure the first end 224 of the bone plate 220 to the second bone (not shown). The first and second fasteners may be, for example, bone screws, which may be locking or non-locking screws. After the bone plate 220 is secured to the first and second bones (not shown), the pin 102, translation member 200, and movement instrument 110 may be removed from the patient. Once the pin 102, translation member 200, and movement instrument 110 have been removed, then the incision in the patient may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A moveable bone plate implantation system, comprising:
   a movement instrument;
   a translation member removeably coupled to the movement instrument; and
   a bone plate detachably connected to the translation member; and
   wherein the movement instrument comprises:
      a base member with a first end and a second end;
      a fixed extension member with a first end and a second end, the first end of the fixed extension member coupled to the second end of the base member;
      a moveable member with a first end and a second end, the first end of the moveable member moveably coupled to the base member;
      a first alignment guide coupled to the fixed extension member and shaped to receive a shaft of the translation member; and
      a second alignment guide coupled to the moveable member;
      wherein the moveable member includes an opening at the first end and the base member is slidingly received within the opening;
      wherein the fixed extension member is directly coupled to the second end of the base member; and
      wherein the moveable member slides from the first end of the base member to the fixed extension member.

2. The moveable bone plate implantation system of claim 1, wherein the shaft includes a first end and a second end, and wherein the translation member further comprises:
   a head portion at the first end.

3. The moveable bone plate implantation system of claim 2, wherein the head portion comprises:
   an engagement groove extending into the head portion and sized to detachably connect to the bone plate.

4. The moveable bone plate implantation system of claim 3, wherein the head portion further comprises:
   a first lip extending away from a bottom portion of the engagement groove and shaped to engage the bone plate.

5. The moveable bone plate implantation system of claim 4, wherein the bone plate comprises:
   an engagement aperture sized to receive the engagement groove of the translation member.

6. The moveable bone plate implantation system of claim 1, wherein the bone plate comprises:
   a body with a first end and a second end;
   at least one first hole positioned near the first end;
   at least one second hole positioned near the second end; and
   an engagement aperture positioned between the first end and the second end for receiving the translation member.

7. The moveable bone plate implantation system of claim 4, wherein the engagement groove is positioned between a proximal end and a distal end of the head portion.

8. The moveable bone plate implantation system of claim 7, wherein the head portion further comprises:
   a second lip positioned at a top of the engagement groove; and
   wherein the second lip extends from the engagement groove, and wherein the first lip extends parallel to the second lip.

9. The moveable bone plate implantation system of claim 8, wherein the engagement groove is recessed within the head portion of the translation member.

10. The moveable bone plate implantation system of claim 9, wherein the bone plate comprises:
    a body with a first end and a second end; and
    an engagement aperture positioned between the first end and the second end,
    wherein the engagement aperture extends from a top surface of the bone plate to a bottom surface of the bone plate.

11. The moveable bone plate implantation system of claim 10, wherein the bone plate has a thickness measured between the top surface and the bottom surface surrounding the engagement aperture.

12. The moveable bone plate implantation system of claim 11, wherein the engagement aperture is configured to have the thickness approximately equal to a height of the engagement groove, and wherein the engagement aperture is configured to have a portion thereof received by the engagement groove.

13. A controlled movement assembly, comprising:
    a translation member, wherein the translation member comprises:
       a shaft with a first end and a second end; and
       a head portion at the first end of the shaft, the head portion comprising:
          a proximal end and a distal end;
          a first dimension perpendicular to the shaft and a second dimension perpendicular to the shaft, wherein the first dimension extends perpendicular to the second dimension, and wherein the first dimension is larger than the second dimension; and
          an engagement groove positioned between the proximal end and the distal end, wherein the engagement groove is recessed within the head portion, and wherein the engagement groove has a height;
          a first lip positioned at a top of the engagement groove; and
          a second lip positioned at a bottom of the engagement groove;
          wherein the first lip and the second lip extend from the engagement groove, and wherein the first lip extends parallel to the second lip; and a bone plate detachably connected to the translation member, wherein when the bone plate is detachably connected to the translation member at least a portion of an interior surface of the bone plate extends into the head portion between the proximal end and the distal end, the bone plate comprising:

a body comprising a first end and a second end; and an engagement aperture positioned between the first end and the second end and extending from a top surface of the bone plate to a bottom surface of the bone plate;

wherein the bone plate has a thickness measured between the top surface and the bottom surface surrounding the engagement aperture; and wherein the thickness of the bone plate near the engagement aperture is approximately equal to a height of the engagement groove;

wherein the engagement groove receives a portion of the engagement aperture;

wherein bone plate has a bottom groove sized to receive the second lip; and wherein the proximal end and the distal end of the head portion of the translation member each have an elongated oval shape.

14. The controlled movement assembly of claim 13, wherein the distal end of the head portion extends below a bottom surface of the bone plate.

15. The controlled movement assembly of claim 13, wherein the engagement groove is shaped to receive an interior sidewall of the bone plate.

* * * * *